United States Patent
Strecker

(10) Patent No.: US 11,918,059 B2
(45) Date of Patent: Mar. 5, 2024

(54) TEXTILE PRODUCT WITH SKIN-CONTACT ELEMENT AND/OR ESTABLISHING EXTERNAL CONTACT WITH THE SKIN-CONTACT ELEMENT, AND METHOD FOR PRODUCING THE SAME

(71) Applicant: TEIIMO GMBH, Gilching (DE)

(72) Inventor: Markus Strecker, Herrsching (DE)

(73) Assignee: Teiimo GmbH, Germering (DE)

( * ) Notice: Subject to any disclaimer, the term of this patent is extended or adjusted under 35 U.S.C. 154(b) by 1051 days.

(21) Appl. No.: 16/304,547

(22) PCT Filed: May 24, 2017

(86) PCT No.: PCT/EP2017/062570
§ 371 (c)(1),
(2) Date: Nov. 26, 2018

(87) PCT Pub. No.: WO2017/202928
PCT Pub. Date: Nov. 30, 2017

(65) Prior Publication Data
US 2019/0297961 A1    Oct. 3, 2019

(30) Foreign Application Priority Data

May 25, 2016 (DE) ...................... 10 2016 109 719.5
Sep. 23, 2016 (DE) ...................... 10 2016 118 001.7

(51) Int. Cl.
*A61B 5/00* (2006.01)
*A41D 1/00* (2018.01)
(Continued)

(52) U.S. Cl.
CPC .............. *A41D 1/005* (2013.01); *A61B 5/282* (2021.01); *A61B 5/291* (2021.01); *A61B 5/6804* (2013.01);
(Continued)

(58) Field of Classification Search
CPC ........ A41D 1/005; A61B 5/291; A61B 5/282; A61B 5/6804; A61B 5/369; A61B 5/318;
(Continued)

(56) References Cited

U.S. PATENT DOCUMENTS 7,697,999 B2 *  4/2010  Axelgaard ........... A61N 1/0456
                                                      600/374
8,032,199 B2   10/2011  Linti et al.
(Continued)

FOREIGN PATENT DOCUMENTS

DE          20305991 U1       7/2003
DE       102004030261 A1      1/2006
(Continued)

OTHER PUBLICATIONS

International Preliminary Report on Patentability for Application No. PCT/EP2017/062570, dated Sep. 18, 2017—6 pages.
(Continued)

*Primary Examiner* — Adam Z Minchella
(74) *Attorney, Agent, or Firm* — Buchanan Ingersoll & Rooney PC

(57) ABSTRACT

A textile product, and methods of using or manufacturing the same, has an electrical skin contact element completely or partially arranged on the inside of the product and at least one extensible conductive textile element mounted on the outside of the product in electrical communication with the skin contact element. In one embodiment, the skin contact element comprises an extensible electrode having an extensible plastic material comprising conductive particles or graphene and is adhered to or printed on the textile product in a region surrounding an opening in the textile product, and is connected to the conductive element adjacent the opening. In another embodiment, the textile product has a conductive region comprising an embedded conductive
(Continued)

polymer material, the conductive element is connected to the conductive polymer material on the outside of the conductive region, and the electrical skin contact element completely or partially penetrates the fabric of the textile product.

32 Claims, 1 Drawing Sheet

(51) Int. Cl.
  *A61B 5/24* (2021.01)
  *A61B 5/282* (2021.01)
  *A61B 5/291* (2021.01)
  *A61N 1/04* (2006.01)
  *A61B 5/318* (2021.01)
  *A61B 5/369* (2021.01)

(52) U.S. Cl.
  CPC ............ *A61N 1/0484* (2013.01); *A61B 5/318* (2021.01); *A61B 5/369* (2021.01); *A61B 2503/10* (2013.01); *A61B 2562/0209* (2013.01); *A61B 2562/12* (2013.01); *A61B 2562/125* (2013.01); *A61N 1/0476* (2013.01)

(58) Field of Classification Search
  CPC ........ A61B 2503/10; A61B 2562/0209; A61B 2562/12; A61B 2562/125; A61N 1/0484; A61N 1/0476
  See application file for complete search history.

(56) References Cited

U.S. PATENT DOCUMENTS

| | | |
|---|---|---|
| 9,589,698 B2 | 3/2017 | Anhalt et al. |
| 9,767,257 B2 | 9/2017 | McBrearty et al. |
| 10,993,635 B1* | 5/2021 | Uy .......... A61B 5/291 |
| 2006/0280322 A1* | 12/2006 | Abe ....... H01R 13/24 381/300 |
| 2008/0091097 A1 | 4/2008 | Linti et al. |
| 2011/0184270 A1* | 7/2011 | Russell ......... A61B 5/6804 600/388 |
| 2012/0238910 A1* | 9/2012 | Nordstrom ......... A61B 5/02438 600/587 |
| 2013/0338472 A1* | 12/2013 | Macia ........ A61B 5/02055 174/255 |
| 2014/0135593 A1 | 5/2014 | Jayalth et al. |
| 2014/0172134 A1 | 6/2014 | Meschter |
| 2014/0246628 A1 | 9/2014 | Anhalt et al. |
| 2015/0040282 A1* | 2/2015 | Longinotti-Buitoni ............... A61B 5/24 2/69 |
| 2015/0250420 A1* | 9/2015 | Longinotti-Buitoni ............... A61B 5/1135 600/534 |
| 2017/0332442 A1 | 11/2017 | Strecker |

FOREIGN PATENT DOCUMENTS

| | | |
|---|---|---|
| DE | 102011101579 A1 | 11/2012 |
| DE | 202015005645 U1 | 9/2015 |
| EP | 2679107 A1 | 1/2014 |
| WO | 2005034663 A1 | 4/2005 |
| WO | 2008022482 A1 | 2/2008 |
| WO | 2009043196 A1 | 4/2009 |

OTHER PUBLICATIONS

International Search Report and Written Opinion for Application No. PCT/EP2017/062570, dated Sep. 18, 2017—3 pages.

* cited by examiner

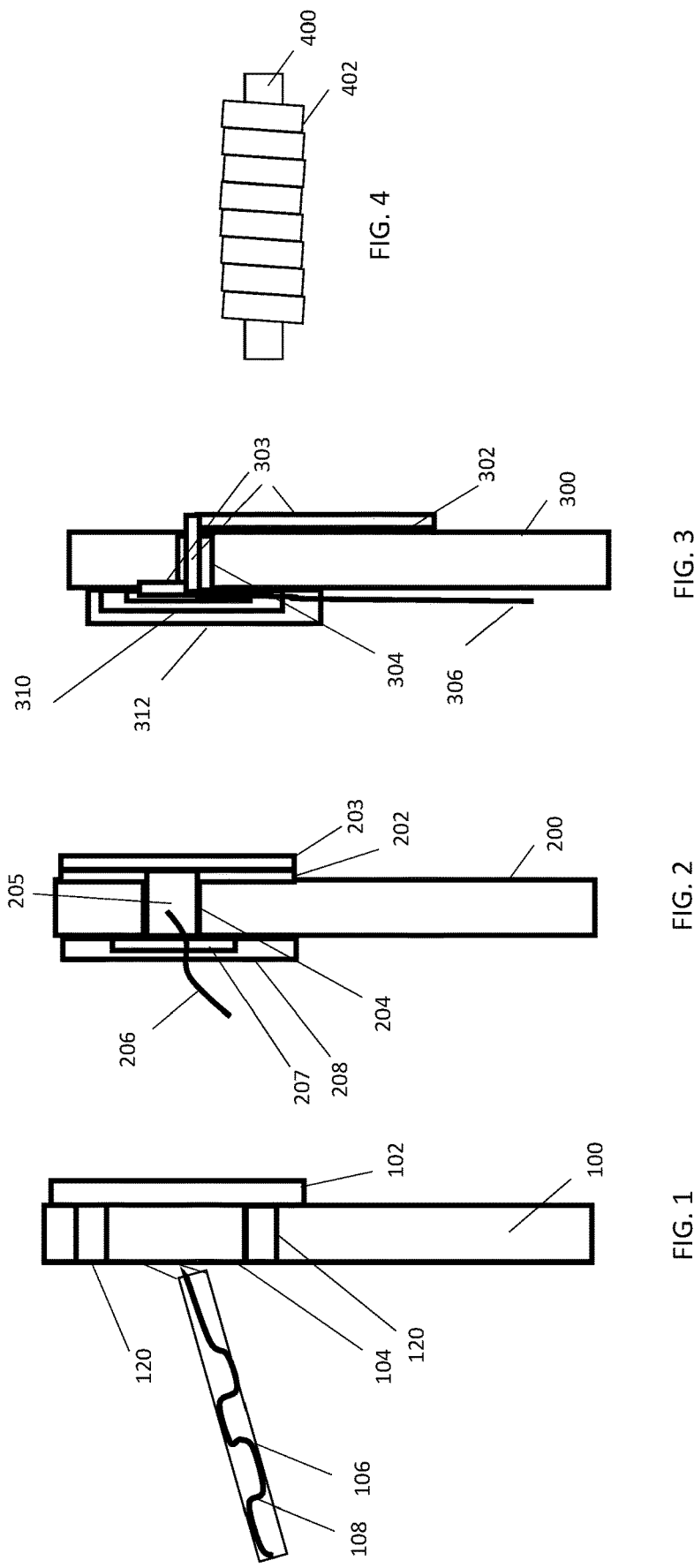

TEXTILE PRODUCT WITH SKIN-CONTACT ELEMENT AND/OR ESTABLISHING EXTERNAL CONTACT WITH THE SKIN-CONTACT ELEMENT, AND METHOD FOR PRODUCING THE SAME

CROSS REFERENCE TO RELATED APPLICATIONS

This application is the National Stage filing of International Appln. No. PCT/EP2017/062570, filed 24 May 2017, which claims priority from German Application DE 10 2016 109 719.5, filed May 25, 2016, and claims priority from German Application DE 10 2016 118 001.7, filed Sep. 23, 2016, the entirety of which applications are incorporated herein by reference for all purposes.

BACKGROUND OF THE INVENTION

Field of Invention

The present invention relates to a textile product with a built-in skin contact element, in particular with a built-in skin contact element and/or a built-in electrode, which, for example, can serve as a sensor for measuring heart rates, respiratory rates, skin temperature and the like. It relates in particular to the connection technology between the skin contact element and an electronic measuring and evaluation unit. In particular, it relates to a shirt or T-shirt. The invention further relates to a process for manufacturing a textile product.

State of the Art

In sports, leisure and healthcare, many people want to record their biometric data and use it to improve their athletic performance or to monitor their state of health. One of the most important parameters is the measurement of heart rate and heart rate variability. Today, these are mainly measured with a chest strap. Devices that measure these parameters via optical sensors are also common today. However, these devices are usually not sufficiently precise.

Many people find the chest strap uncomfortable. Marathon runners often avoid it because of friction and irritation of the skin.

There is a range of T-shirts with integrated electrodes on the market. These are usually connected to a conventional electronic module. This is typically placed between or next to the electrodes and connected to the shirt by push buttons. Especially for ball players such as football players this arrangement is unthinkable.

The shirts existing today usually have electrodes made of conductive polymer material that is not extensible and thus forces the shirt to move against the body. The shirt does not harmoniously follow all movements. Further, there are versions of shirts with an electrode made of silver-coated textile material. However, this material has substantial restrictions regarding their durability. When washing, for example, it is sensitive to chlorine components in the washing agent. Sweat in combination with weak electrical signals is sufficient to quickly impair the function of the silver coating. Silver-coated fabrics further have significant functional limitations because they require a minimum amount of moisture to make good contact with the skin and are not functional when dry. In addition, these are usually very expensive and complex in manufacturing.

Electrodes are applied to persons, for example, to measure an ECG (electrocardiogram). An ECG is an oscillogram by which muscle activities, including those of the heart muscle, are represented electrically. The basic principle of ECG measurement is based on the measurement of tension gradients between human extremities. The ECG measures the potential distribution on the surface of the human body resulting from the temporal superposition of all nerve signals in the heart.

For ECG and pulse measurement in medicine and sports, electrical signals must be read from the skin surface. Long-term ECGs are particularly important for the diagnosis of cardiac arrhythmias, but can only be performed up to approx. 24 hours using conventional adhesive electrodes. In sports, chest straps are used for pulse measurement, which are not only disturbing, but usually work reliably only when a conductive gel is used.

The disadvantage of the ECG procedure is that a gel must be applied to the patient's chest first in order to establish ohmic contact between the electrodes and the skin. Then the patient must lie still to make sure that no electrode drops off.

The signal to be measured is in the range of a few millivolts. Analog frontends (AFEs) and DSPs then amplify, digitize and filter the analog, bioelectrical sensor signals. Once the signal processing has processed these data accordingly, they can be transmitted for example via Bluetooth. Depending on the field of application in sports and fitness or in real-time telemedicine, various wired or wireless transmission paths of bioelectrical signals to a wristband or watch, or even directly over a longer distance, are possible, which can then be evaluated on the PC for self-monitoring of one's own physical fitness or for health control by a doctor.

With the help of textile or plastic (e.g. PA, PU or silicone) based sensors, ECG and pulse signals could be measured without temporal limitations and without causing skin irritations. Such electrodes consist of textile conductors, for example wrapping yarns, fibre yarns with stainless steel content or conductively coated yarns.

These yarns have a textile character because the low metallic content is not felt, and they can be woven, embroidered or knitted like any other yarn. These textile electrodes can be integrated into a sensor textile product to measure ECG or pulse. This ensures that they are positioned correctly at the same time; it is difficult to apply them incorrectly.

Another state-of-the-art product, for example, is a stimulation current device that can be applied to the wrist and the like. For certain parts of the body, such as the wrists, special electrodes are needed that gently fit and enclose everything. This goal is achieved by using elastic cuffs into which silver yarn has been incorporated. This transmits the stimulation current evenly and has a long durability.

The disadvantage of these products, however, is that the electrodes as such are not extensible, or sensitive to chlorine or irritate the skin, or are often very thick and are not extensible. Furthermore, the electrical connection regions usually have to be encapsulated with non-extensible materials or encapsulated relatively thick. This leads to a significant restriction in the usability and wearing comfort of these products.

Problems to be Solved by the Invention

It is the object of the present invention to provide a textile product which has one or more skin contact elements such as electrodes and/or (flat) sensors or actuators to measure body activity, temperature or to transmit electric current or other stimuli such as vibrations from the skin or to the skin of a wearer and which offers advantages in wearing comfort.

SUMMARY OF THE INVENTION

The problem is solved by providing the textile product according to the invention.

The subject of the present invention is in particular the following:

[1] A textile product having at least one electrical skin contact element, in particular an extensible electrode. In particular, it is a base layer textile product, i.e. a textile product worn directly on the skin.

In this context, any element which comprises active or passive electrical components such as electrodes or sensors and which is configured to be in direct or at least substantially direct contact with the skin of a wearer of the textile product in order to measure physical or chemical properties of the skin or to transmit stimuli to the skin is to be referred to as an electrical skin contact element.

[2] A textile product according to [1], wherein the extensible electrode comprises a extensible plastic having conductive particles or other conductive material.

In the context of the present invention, the term "conductive" means "electrically conductive".

[3] A textile product according to [1] or [2], wherein the extensible plastic is silicone. This means that the extensible electrode or the extensible material preferably contains silicone. In one version, the elastic part of the extensible electrode is made of silicone.

[4] A textile product according to one of the above points [1] to [3], wherein the conductive particles contain carbon and are preferably at least partially carbon particles. Particularly preferred are all conductive particles made of carbon.

[5] A textile product according to any of the above points [1] to [3], wherein the other conductive material is graphene.

[6] A textile product according to any of the above points [1] to [5], wherein the extensible electrode is partially or completely disposed on the inside of the textile product or the electrode penetrates the fabric of the textile product.

[7] A textile product according to any of the foregoing points [1] to [6], wherein the extensible electrode consists of or contains silicone admixed with conductive carbon particles.

[8] A textile product according to one of the above points [1] to [7], wherein the extensible electrode is attached to the textile product with an adhesive, preferably a silicone-based adhesive, or is attached to a textile comprising hot-melt adhesive, for example PU.

[9] A textile product according to one of the above points [1] to [8] in which the extensible electrode is connected via a conductive, preferably extensible material, to a conductive element, preferably an electrically conductive tape, which is more preferably extensible. A favourable example of a conductive, extensible material in this context is silicone.

[10] A textile product according to any of the above points [1] to [9], the conductive element comprising one or more metallic filaments (hereinafter also referred to as wires or wires or conduits) arranged in a wavy or sinusoidal manner in a extensible textile tape, or wherein the conductive element comprises one or more extensible cores, e.g. extensible filaments (e.g. rubber filaments), wrapped with one or more metallic filaments. The metallic threads can be made of copper or silver, for example, or an alloy containing copper or silver, or copper threads coated with silver. They are preferably coated with a non-conductive lacquer, which can have different colours, so that the individual lines can be easily identified and suitably connected.

[11] A textile product according to any of the above points [1] to [10], wherein the conductive element is mounted on the side of the extensible electrode remote from the body of the wearer.

[12] A textile product according to one of the above points [1] to [11], wherein in the region of the connection between the extensible electrode and the conductive element, an insulation consisting for example of or containing a non-conductive silicone is applied to insulate the textile product in this region to the outside.

[13] A textile product according to one of the above points [1] to [12], wherein the conductive element does not extend at least on the side of the textile product facing the body of a wearer and preferably on the outside of the textile product facing away from said body.

[14] Textile product which has a preferably planar, more preferably flat (i.e. only slightly raised, nor more than 2 mm, preferably not more than 1 mm) sensor, in particular a pressure, temperature or strain sensor, which sensor may be extensible (and then has other properties than the extensible electrode of the point [1]), but does not have to, and is arranged partially or completely on the inside of the textile product, wherein the sensor is connected via a conductive, preferably extensible material to a conductive element, preferably an electrically conductive strip, which is more preferably extensible. The conductive element is mounted on the side of the sensor facing away from the body of the wearer. The sensor can comprise an electrode configured for skin contact, but can also be formed as a sensor for measuring moisture or pH, as an electrochemical or optical sensor, which can be used as an alternative or supplement to the extensible electrode material.

[15] Textile product according to the preceding point [14], wherein the sensor is attached to the textile product with an adhesive, preferably a silicone based adhesive or a hot melt adhesive, e.g. made of PU.

[16] A textile product according to any of the foregoing points and [15], the conductive element comprising one or more metallic filaments (hereinafter also referred to as wires or wires or leads) which are arranged in a wavy or sinusoidal manner in a extensible textile tape, or wherein the conductive element comprises a extensible core, e.g. a extensible filament (e.g. rubber filament), which is wound with one or more metallic filaments. The metallic threads serve as leads and can for example be formed of copper or silver or an alloy containing copper or silver or a copper wire coated with silver. They are preferably coated with a non-conductive lacquer, which can have different colours, so that the individual cables can be easily identified and connected in a suitable manner.

[17] A textile product according to one of preceding points to [16], wherein the sensor has a sensor surface arranged on the inside of the textile product and adapted to contact the skin of a wearer. Further components of the sensor may be housed; the electrical connection to the conductive element (or a plurality thereof) is made via contacts located on the outside of the sensor.

[18] A textile product according to one of the above points [14] to [17], wherein the sensor comprises a single conductive element with preferably a plurality of metallic leads through which all necessary information is transmitted as electrical signals.

[19] A textile product according to one of the above points [14] to [17], wherein the sensor comprises two or more conductive elements such that a changing property of the sensor, in particular a change in strain, can be measured between the conductive elements.

[20] A Method for manufacturing a textile product, preferably according to one of the above points [1] to [17], comprising the following steps:
Step (a) in which an opening is produced in a textile material;
Step (b) in which an adhesive is applied around the opening on one side of the textile material;
Step (c) in which a support covering the opening, preferably a textile patch, is provided on the other side of the opening;
Step (d) in which the extensible electrode or other sensor is applied to the adhesive and the support;
Step (e) in which the support is removed;
Step (f) in which, with the aid of a conductive, preferably flexible material, a connection is made between the extensible electrode and metallic wires of an extensible conductive element, preferably the metallic core of an extensible ribbon conductor;
Step (g) in which this connection is covered with non-conductive material.

[21] A method according to [20], wherein the adhesive is a cross-linkable adhesive cured according to step (e), wherein the conductive material is preferably a silicone and/or the non-conductive material is also preferably a silicone. The term "hardening" is to be understood here in particular also as cross-linking and/or drying processes. In advantageous embodiments of the invention, a material is used which remains flexible and/or extensible even after hardening, for example silicone.

[22] Method according to [20] or [21], where the opening is an opening or a slot.

[23] Process for producing a textile product, preferably according to one of the previous points [1] to [19] comprising the following steps:
Step (1) in which an opening is produced in a textile material;
Step (2) in which an extensible electrode or other sensor is provided as defined in the above-mentioned points, bonded by means of a conductive material to metallic wires of an extensible conductive element, in particular the metallic core of an extensible conduction band;
Step (3) in which part of the extensible electrode or other sensor is inserted through the opening and then adhered to the inside by means of a non conductive material.

It should be noted that due to the special material properties of the extensible electrode, it is generally not permitted to sew onto the electrode. Here, the inventors suggest that the electrode should be guided outwards on one side through an opening and then glued to the outside so that the conductive element can be sewn next to the electrode.

In an alternative process, an assembly of electrode and conductive element is produced first. This is then glued in place and overlaminated. Adhesive is applied to the inside of the textile, then the conductive element is inserted through an opening and the electrode is then glued in (with a heat press), then it is covered from the outside with textile or rubber material or tape. With regard to the latter variation, it is suggested that one end of the electrode be led to the outside, where the contact to the conductive element is made or comes to rest. This contact region is then covered.

[24] Method according to [23], where the conductive material is a silicone and the non-conductive material is a silicone.

[25] Method according to [23] or [24], where the opening is a slit cut into the textile material.

[26] Method for producing a extensible textile product, preferably according to one of the above points [1] to [13], characterized by the following steps:
Step (i) in which at least part of a extensible textile material is impregnated with electrode material or conductive material which is extensible after curing and preferably contains conductive particles.
Step (ii) in which the part of the textile material which has been impregnated with electrode material or conductive material is joined on the outside to the metallic core of a conductive ribbon;
Step (iii) in which the electrode material is hardened or the conductive material is hardened in such a way that the resulting electrode passes through the textile material and can be contacted on the outside.

[27] Method according to [26], wherein the plastic material is a silicone.

[28] A method according to [26] or [27], wherein the impregnation is carried out using at least one measure selected from the use of a solvent, applying negative or positive pressure to the textile material, stretching the textile material and heating the plastic material.

[29] A method according to any one of points [20] to [28], wherein a textile product is manufactured according to any one of points [1] to [19].

[30] A textile product according to any of the foregoing points [1] to [13] obtainable by the following process:
Step (i) in which a extensible textile material is compounded, preferably impregnated, with extensible plastic containing conductive particles.

[31] Textile product according to [29], the compounding being an impregnation, optionally using a solvent.

[32] A textile product according to [30] or [31], wherein before step (i) the extensible textile material is stretched and after step (i) the stretched textile material is relaxed and optionally the solvent is removed.

[33] Textile product producible by a process according to one of the points [20] to [29].

[34] Textile product according to one of the points [1] to [19] or [30] to [33] or process according to one of the points [20] to [29], wherein the elastic extensibility of the electrode is at least 10%, preferably at least 20%, more preferably at least 30%. Even more preferably, the ductility and elastic properties of the electrode and the textile material are identical or differ by not more than 50%, 30%, preferably by not more than 20%, more preferably by not more than 10%. It is always advantageous if the electrode is more flexible than the textile material, because then it cannot be overstretched under any circumstances, even under extreme stress. Alternatively, however, the textile material can be more extensible instead; this will be the case in many cases for practical reasons: many of the possible electrode materials are less extensible than conventional, usable textile materials. In this case, however, the elasticity difference should normally not exceed 30%.

[35] A textile product referred to in points [1] to [19] or [30] to [34] which is a garment, preferably a garment intended for sporting activities and in particular a shirt, undershirt, body, bodice or a cap or sports pants. In addition to its usual basic function, this garment is intended to monitor body data and is mainly used in the health sector, for sports activities and/or for medical purposes.

[36] Use of a textile product according to one of the points [1] to [19] or [30] to [35] to measure heart rate, to apply a stimulation current, to stimulate muscles, to measure an electrocardiogram or to measure brain waves. In these cases, the textile product will usually have at least two extensible electrodes.

[36] Use according to point [35] to create an electrocardiogram. This usually requires that more than two sensors or electrodes exist in the sensor textile product according to the invention,

[37] Use of a textile product according to one of the points [14] to [19] for measuring the respiratory rate, the skin temperature, the pressure between the textile product, in particular a shirt, and an element or body of the wearer or the pressure exerted by the wearer of the textile product against a support or other surface or vice versa.

[38] Process for manufacturing a textile product comprising the following steps:

Step (1), a region in the textile is impregnated with a polymer material (preferably silicone) so that this impregnated region is electrically conductive and can conduct a current/voltage from the inside to the outside (or vice versa), Step (2), a sensor is attached to the inside of the textile product (e.g. shirt).

Step (3), an extensible conductive element is glued conductively to the region from the outside, wherein the conductive element can be a strip with metallic conductors or another type of conductive channel conductor.

[39] Method for producing a textile product in accordance with [38], in which the textile is impregnated with non-conductive polymer (preferably silicone) around the conductive region which has been produced by impregnation, so that a non-conductive ring (insulation) is produced around the conductive region and preferably a complete insulation (3-dimensional) of the "through-plating" formed in step 1 is produced.

[40] A textile product comprising a conductive region and a ring of a non-conductive polymer disposed around the conductive region, preferably obtainable by a process according to one of points [38] or [39].

Advantages of the Invention

The main advantage of the invention and of its configuration with an extensible electrode is that, due to the extensibility of the extensible electrode, the wearing comfort of the textile product is not limited by the presence of the electrode, or at most imperceptibly or insignificantly limited.

Another significant advantage is that the electrode is configured or the sensor is arranged in such a way that it can be contacted on its outside. Since this outside is usually not located inside the textile product, the electrical cables can be routed on the outside of the textile material, which increases wearing comfort extremely and does not cause the electrical cable to rub against the skin.

In addition, the textile product according to the invention has the advantage that the manufacturing technology is largely compatible with various standard manufacturing methods in textile manufacturing and can be applied in addition to these in a convenient manner. Among other points, the manufacturing costs can thus be reduced.

BRIEF DESCRIPTION OF THE DRAWINGS

FIG. 1 is a cross sectional schematic drawing illustrating a relevant portion of one embodiment of the invention.
FIG. 2 is a cross sectional schematic drawing illustrating a relevant portion of another embodiment of the invention.
FIG. 3 is a cross sectional schematic drawing illustrating a relevant portion of another embodiment of the invention.
FIG. 4 is a plan view schematic drawing illustrating a relevant portion of an exemplary conductive element.

DETAILED DESCRIPTION OF THE INVENTION

Conductive Plastic

Silicones are polymeric compounds that occupy an intermediate position between inorganic and organic compounds. While carbon atoms form the molecular chain in completely organic polymers, silicon is the molecular chain in silicones. The typical characteristic of silicones is the siloxane bond Si—O—Si, which is why the term polysiloxane is often used. Silicones obtain their organic character from the hydrocarbon groups bonded to the silicon atoms. These are mostly methyl groups, more rarely ethyl, propyl, phenyl and other hydrocarbon radicals.

The silicones can be liquid to viscous or solid, depending on the chain length, degree of branching and type of the hydrocarbon groups bound to the silicon. Most silicones are water repellent, electrical insulators and resistant to acids. They are not harmful to health. Silicone rubbers are substances which can be transferred into the rubber-elastic state and which contain poly(organo)siloxanes with groups accessible for cross-linking reactions. Hydrogen atoms, hydroxy groups and vinyl groups, which are located at the ends of the chain but can also be incorporated into the chain, are predominantly considered as such. Silicone rubbers usually contain reinforcing substances and fillers, the type and quantity of which significantly influence the mechanical and chemical behavior of the silicone elastomers produced by crosslinking. Silicone rubbers can be colored with suitable pigments.

A distinction is made between cold (RTV) and hot (HTV) crosslinking silicone rubbers (RTV=room temperature crosslinking, HTV=high temperature crosslinking) depending on the necessary crosslinking temperature. HTV silicone rubbers are plastically deformable materials. They very often contain organic peroxides for crosslinking. The elastomers produced from this by crosslinking at high temperatures are heat-resistant products that are elastic between −40 and 250° C. They are used, for example, as high-quality sealing, damping, electrical insulation components, cable sheathing and the like.

The electrically conductive elastic polymers used in this invention are not particularly restricted as long as they have the desired elastic properties. However, they are preferably manufactured on a silicone basis.

For example, they consist of silicone and/or fluorosilicone as well as conductive particles.

The conductive material covers a range from carbon particles such as carbon black to metal particles such as silver. The conductive particles introduced into the polymer, e.g. silicone, are for example metals such as iron, silver, copper or gold, or carbon-containing particles, e.g. in the form of graphite, graphene, carbon fibres or nanotubes. Conductive polymers such as polypyrrole or polythiophene are also possible.

In this invention, the term "particle" means particles with a diameter of 10 nm to 10 μm, preferably 100 nm to 5 μm.

Silicone elastomers (silicone rubber), which have preferably been made electrically conductive by the incorporation of carbon, are preferably used as electrode material and as conductive material.

For example, a mixture of carbon nanotubes and silicone polymers with high electrical conductivity can be used. These plastics are both electrically conductive and flexible as well as extensible. For example, a proportion of up to 20 percent by weight of single-walled nanotubes does not reduce the mechanical flexibility and softness of the polymer. Rubber is a extensible polymer based on dimethyl siloxane. It is used to coat a second thin plastic layer in which the electrically conductive nanotubes were previously distributed. In order to avoid the inconvenient clumping in a mixture of the tiny carbon particles in a polymer, the nanotubes are first distributed in an ionic liquid (1-butyl-3-methylimidazoliumbisimide). This substance effectively prevents the tubes from attaching to each other. The resulting black nanogel is then compounded with another liquid polymer (vinylidene fluoride hexafluoropropylene) and the resulting mixture is sprayed as a thin film onto a glass substrate. This composite material is then bonded with the extensible silicone rubber to form the desired end product. This material shows good conductivity in its unstretched state and can be pulled apart many times without decreasing its conductivity. This makes it relatively easy to produce very hard-wearing materials for the textile products according to the invention.

Alternatively, graphene can also be incorporated to achieve the required conductivity.

The term "extensible" used in this invention is identical to the term "elastic". According to the general definition, elasticity is the property of a body or material to change its shape under the action of a force and to return to its original shape when the force acting on it ceases. In the present invention this means, for example, that a textile material or an electrode can be stretched in at least one direction by a tensile load and returns to its original shape after the tensile load has ended. In this invention, the elastic properties, such as elasticity and elastic limit, of the textile material and the electrode are preferably identical.

The term "extensible electrode material" used here refers to a composition containing said conductive particles and said extensible plastic. The extensible plastic is selected so that, after any cross-linking operation being carried out, it is extensible and suitable for the present invention. The extensibility is preferably at least 10%, more preferably at least 30% and even more preferably at least 50% in at least one, preferably both, surface directions.

The electrode material used in this invention is not particularly restricted as long as it can fulfil its function as an electrode. Preferably, the electrode material contains an elastic plastic. A particularly preferred material is silicone, which contains electrically conductive particles. The electrode is particularly preferably made of a silicone loaded with carbon particles and/or has a thickness of 100 to 500 μm.

The hardenable plastic material used in this invention, which is added to the textile material, can be any plastic material that can be hardened by heating, for example. Preferably this plastic material is a silicone.

The adhesive used in this invention is not particularly restricted as long as the desired materials can be bonded and firmly bonded to it. The adhesive is preferably a hardenable plastic material that can be hardened by heating, for example. Preferably this plastic material is a silicone. Instead, it is also possible to use a hot-melt adhesive which is applied to the textile material and does not stick at ambient temperature. It can be transferred to the adhesive state in a hot press or the like. The advantage of such an adhesive is that excess adhesive, which is not covered by the materials to be bonded on both sides no longer shows any adhesive activity as soon as ambient temperature and pressure prevail again. Materials for hot-melt adhesives are known to experts. PU (polyurethane), for example, can be used.

In one version, the electrode consists of a silicone material. This is charged with carbon particles and is therefore electrically conductive. The thickness of the electrode is in the range from 100 to 500 μm, preferably 250 to 350 μm.

Insertion of the Electrodes or Other Sensors

The electrode material is applied to a surface in a squeegee process and a sheet, i.e. a thin, flat structure, is produced. This sheet is then separated so that platelets with a length and width in the centimeter or millimeter range and a thickness in the specified range, for example about 300 μm, are produced.

The electrodes and sensors can be inserted in several ways.

In the first version, depicted in FIG. 2, an opening 204 is cut into the fabric 200 of a textile material. An adhesive, not yet cross-linked, non-conductive silicone 202 in the size of the electrode is applied to the fabric of the textile material. The opening is lined with a piece of fabric as a backing (not shown). This back-lining material is removed before the silicone dries, usually after, but also sometimes before the electrode or other sensor is glued on. The electrode or the sensor 203 is placed in the not yet cross-linked silicone and thus glued. If the sensor has a one-sided sensor surface, it should point upwards so that it is on the inside of the textile product in its finished state. In the area of the opening, a conductive silicone 205 is used to create a connection to the metallic core of a extensible conductive ribbon. This ribbon can be a fabric ribbon. This contact region is then covered with non-conductive silicone 207 and covered with a fabric patch 208. The silicone materials that have not yet been cross-linked are then cross-linked by heat or light and thus solidified.

In the present application, the terms "cross-linking" and "hardening" of polymers are used synonymously. In the second version, depicted in FIG. 3, only a slit 304 is cut into the textile material 300. The electrode/sensor 303 is bonded by means of a conductive silicone 310 to the metallic core of an extensible conductive tape 306, and a textile patch 312 is applied over the bonded area. The electrode or part of the electrode is now pushed through the slit and then bonded to the inside using a non-conductive silicone 302.

A third type, depicted in FIG. 1, only relates to the configuration of the invention in which the textile product is equipped with a extensible electrode 102. In this embodiment, one region of the fabric is preferably stretched slightly and then covered in all cases with conductive silicone instead of providing an opening or slot as in the first two versions. For example, a vacuum is then applied to the area below the silicone on the back of the fabric, so that the conductive silicone is soaked into the fabric structure. This creates a region 104 of the fabric that is saturated with conductive silicone. This creates a contact from the inside to the outside of the fabric. On the outside a contact to a supply line is established before the conductive silicone hardens. For example, conductive extensible ribbons 106, which are described in more detail below, are used for this purpose. In some examples of the invention, a non-conductive silicone can be applied to the inside via a window process after the silicone is cured. The window saves the area of the conductive silicone. Then a conductive electrode can be glued in.

The process described above can also be carried out with another conductive polymer material.

The preferred textile material according to this invention is a single-layer textile, which can further be knitted.

In one embodiment, a ring 120 with non-conductive silicone (or other non-conductive polymer material) is added around the conductive silicone (or other conductive polymer material) 104, which serves as a "through-hole", in order to insulate the connection to the outside.

In order to ensure a secure contact between the electrode and the contact structure, a small amount of conductive silicone is optionally applied over the conductive material. Non-conductive silicone is now applied to the outside and covered with a material.

In some examples of the invention, the provision of the conductive electrode to be bonded can be dispensed with since the silicone penetrating the material has sufficient conductivity to conduct the electrical signals from the inside to the outside, and thus already functions as an electrode as such. In the third embodiment, a textile product is obtained in which the electrode and/or the conductive material is an integral part of the textile product by the electrode and/or the conductive material microscopically penetrating the fabric of the textile product.

The penetration of the extensible electrode material containing the conductive particles and the extensible plastic into the extensible textile material can be facilitated by performing one or more of the following actions:

(a) The electrode material may be diluted by adding a solvent or additional solvent to it so as to reduce the viscosity of the material and facilitate its penetration into the pores of the textile material. The solvent can be selected to influence the hydrophobicity of the electrode material according to the needs and properties of the textile material.

(b) The textile material can be stretched so that its pores are enlarged and thus the electrode material can penetrate more easily. This measure is particularly recommended where the conductive particles contained in the electrode material are relatively large. Stretching can prevent these particles and/or the extensible plastic from being distributed unevenly in the textile material. It is therefore preferable that the particles are as small as possible and especially preferred not to exceed a diameter of 2 μm, more preferred not to exceed 100 nm.

(c) The penetration of the electrode material can be facilitated by a measure in which an external force acts on the materials. For example, a negative pressure can be applied to one side of the textile material, causing the penetration of the electrode material on the other side of the textile material. Another example is the printing of the electrode material.

(d) The electrode material can be heated to reduce its viscosity.

An essential feature of the electrode arrangement of the present invention is that the electrode is guided from the inside of the textile material to its outside.

In addition, the connecting cable is routed on the outside of the textile product, which increases wearing comfort for the user. Particularly preferred is that all parts that are applied, i.e. represent a raised area on the textile product and can thus disturb, are arranged on the outside. Another feature is the creation of a flexible electrical connection from the inside to the outside, which preserves the flexibility and stretchability of the textile.

The electrode that can be used in the textile product according to the invention serves to measure electrical currents on the body of the wearer of the textile product, to stimulate the body via electrical impulses/currents/voltages. Alternatively, a sensor can be incorporated into the textile product to measure skin temperature, respiration or the pressure exerted by the body of the wearer of the textile product against an opposing surface at the position of the sensor. The electrode or sensor is preferably located on the inside of the textile product, i.e. on the side which corresponds to the body of the wearer of the textile product is facing. The electrode is preferably located flush on the inside of the textile product. Contacting, on the other hand, takes place on the side of the textile product facing away from the wearer.

Conductive Element

The electrodes or sensors are connected to the measurement and evaluation system via a conductive element. The conductive element is characterized by the fact that although metal is used as the conductor on the one hand, the conductive element can be stretched on the other hand without the risk of damaging the metal, so that the conductive element can also stretch when the textile product is stretched, without this having disadvantages regarding the transport of the electrical information.

In the first example, depicted in FIG. 1, the conductive element is a conductive tape, preferably a conductive textile tape 106.

This textile tape or ribbon 106 is equipped with a strand (also called a core 108). The latter is preferably woven in a sinusoidal or wave-like manner. A special feature here is that several, e.g. four, ten or 16 or e.g. also 40 individual insulated wires (metallic conductors) are contained and the lacquer insulation preferably has several different colours in order to be able to distinguish between wires carrying different electrical information. The ribbon is preferably configured to cover the metallic conductors on one side in such a way that they cannot be seen. On the other side they can be visible, but of course they can also be "hidden" on this side. In alternative versions of the invention, a sheathing or an insulation extruded from PFA material, for example, can be used instead of lacquer insulation.

The tape can, but does not have to, be extensible. With suitable weaving techniques, for example, an elasticity of approx. 0% (non-extensible) to 100% can be achieved. In the invention's embodiments, the elasticity is preferably 5 to 70%.

The width and thickness of the ribbon is preferably configured in such a way that it can be sewn over with a flatlock machine and thus fastened. The electrical conductors are usually arranged sinusoidally or wave-like in the middle with a distance to the edges so that they are not damaged when the ribbon is sewn in at the edges. This means that the dimensioning of the ribbon is adapted for the use of a flatlock sewing machine, in particular a sewing machine with two needles. With a flatlock sewing machine, a so-called flat seam or flatlock seam can be produced. This is above all an ornamental seam. It has the advantage that it is flat and therefore does not interfere with seam allowance in tight-fitted clothing.

Instead of such a ribbon, for example a extensible thread or a woven ribbon made of extensible threads, can be provided in a second variant, depicted in FIG. 4, whereby the extensible thread 400 or individual or groups of the extensible threads of the ribbon are wrapped with one or more metallic threads 402. Rubber threads, for example, can be used as threads. If a ribbon is used, the same as for the ribbon with strand or core applies with regard to its dimension and the ability to be sewn in.

As an alternative to attaching the tape by sewing, the tape or thread can also be glued in, stitched in or laminated on. The latter is possible, for example, with the aid of an adhesive which is activated by raising the temperature. In these cases, the dimension of the ribbon is not limited.

The ribbons preferably include fabric ribbons and electrical conductors applied to one side of the fabric ribbon. The ribbons are then applied to the textile product in such a way that the fabric ribbons face the outside and the electrical conductors face the textile product, so that the electrical conductors are not visible.

In this invention, the term "stranded wire" means an electrical conductor consisting of thin individual wires and being therefore easy to bend. Copper is mainly used as a conductor in electrical cables. Individual wires of the strand (some, e.g. four or 10, up to several hundred) can be enclosed by a common insulating sheath. The metal of the electrical conductors contained therein ("small wires") preferably consists of copper, silver or an alloy which preferably contains copper or silver as a component. A copper wire coated with silver can also be used. This increases the bending strength of the conductor and/or its flexibility. Stainless steel conductors are used in other advantageous embodiments of the invention.

The advantage of stranded conductors and extensible cores wrapped with small wires is that the risk of conductor rupture due to bending is considerably lower than with solid wire conductors with the same cross-section. Therefore, stranded conductors and conductors made of extensible cores wrapped with small wires are particularly suitable for use in textiles where frequent movement or vibration stress occurs. Depending on the required flexibility and degree of stress, fine or very fine stranded conductors are used.

In this invention, a multicoloured stranded wire is preferably used, for the insulation of which lacquers with typically up to four colours are used. The wires insulated with different colours can be controlled separately. There may preferably be 4 signal lines per strand.

This type of construction makes it possible to attach electrodes or other sensors largely freely with maximum comfort for the user and to decouple the position of the electrodes/sensors and the electronics to a large extent. The configuration of the ribbons plays a role here. In order to transmit weak electrical signals over a long distance without interference, a coaxial cable can be used, but this is expensive. Another possibility is the use of cables with twisted pairs of wires. These are cable types in which the cores are twisted together in pairs. Pairs of cores can be stranded in one cable with different twist strengths and different direction of rotation. Twisted pairs of cores offer better protection against external alternating magnetic fields and electrostatic influences than cores which are only guided in parallel. By twisting the wire pairs, influences from external fields cancel each other out to a large extent. Twisted pairs of wires are subjected to symmetrical signals in order to be able to form the difference between the signals of the two wires at the far end of a (longer) cable section and thus to reconstruct the transmitting signal as good as possible at the receiving location.

The extensible ribbons allow the use of a twisted pair of cores in which a bundle of strands with different colours has been inserted. The strand bundle is twisted and can therefore carry different signals. The same applies to small wires which are wound spirally around an extensible core. In this way, any radiated interference can be filtered out with a specific structure.

The use of metal as a conductor also means that it is possible to work at low-resistance. Despite the use of metal, the structure of the ribbons and filaments with a wavy, sinusoidal or spiral shape means that the ribbons or filaments are highly extensible, making them more suitable for the intended purpose than the configurations according to the prior art.

The invention claimed is:

1. A textile product configured to be worn on a body of a wearer, the textile product having an outside surface facing away from the wearer's body and an inside surface configured for skin contact with the wearer's body, the textile product comprising:
  at least one opening in the textile product extending between the outside surface of the textile product to the inside surface of the textile product, the opening defining an area;
  one or more integrated sensors, each having an inside portion disposed on the inside surface and an outside portion disposed on the outside surface:
    the inside portion comprising an electrical skin contact element having a first side defining a first area larger than the area defined by said opening and configured for skin contact with the wearer's body over an entirety of the first side having the first area, and a second side opposite the first side and defining a second area equal to the first area, said electrical skin contact element partially or completely arranged on the inside surface of the textile product with the second side adhered to the inside surface of the textile product around the area defined by said opening, the electrical skin contact element formed as an extensible electrode over the entirety of the first side, and including an extensible plastic material comprising conductive particles or graphene; and
    the outside portion comprising at least one extensible conductive element mounted on the outside surface of the textile product and directly connected to the second side of the skin contact element adjacent the opening via a connection consisting of a conductive polymer disposed in the area defined by the opening.

2. The textile product of claim 1, further comprising non-conductive polymer disposed on the outside surface of the textile product around said opening and covering said conductive polymer, and a fabric patch covering said non-conductive polymer disposed on the outside surface of the textile product.

3. The textile product of claim 1, wherein said electrical skin contact element is partially or completely arranged on the inside surface of the textile product with the second surface adhered to the inside surface of the textile product surrounding the area defined by said opening.

4. The textile product of claim 1, wherein the second side of said electrical skin contact element partially or completely arranged on the inside surface of the textile product is adhered to the inside surface of the textile product with a non-conductive adhesive.

5. The textile product of claim 4, wherein the non-conductive adhesive comprises non-conductive silicone.

6. The textile product of claim 1, wherein the electrical skin contact element comprises more than one layer.

7. The textile product of claim 6, wherein the electrical skin contact element comprises at least one layer comprising the conductive particles or graphene and at least one layer comprising silicone rubber.

8. A textile product configured to be worn on a body of a wearer, the textile product comprising a fabric having an outside surface facing away from the wearer's body and an inside surface configured for skin contact with the wearer's body, the fabric having pores extending from the outside surface of the fabric to the inside surface of the fabric, the textile product comprising:
one or more integrated sensors, each having an inside portion disposed on the inside surface and an outside portion disposed on the outside surface:
the inside portion comprising an electrical skin contact element having a first side configured for skin contact with the wearer's body and a second side opposite the first side, the electrical skin contact element partially or completely arranged on the inside surface of the fabric with the second side adhered to the inside surface of the fabric, the electrical skin contact element comprising an extensible electrode and including an extensible plastic material comprising conductive particles or graphene;
the outside portion comprising at least one extensible conductive element mounted on an outside of the fabric; and
a conductive region of the fabric comprising a conductive polymer material embedded in the pores of the fabric in an area of the fabric extending between the inside surface of the fabric and the outside surface of the fabric,
the at least one extensible conductive element directly connected to the conductive polymer material on the outside of the fabric in said conductive region, the conductive region providing a sole electrical connection configured to conduct a current or voltage between the at least one extensible conductive element and the electrical skin contact element through the fabric of the textile product between the inside surface of the fabric and the outside surface of the fabric.

9. The textile product of claim 8, further comprising a ring of a non-conductive polymer disposed around the conductive region.

10. The textile product of claim 8, wherein the conductive polymer material of the conductive region is a same material as the extensible plastic material of the at least one skin contact element.

11. The textile product of claim 8, wherein the extensible plastic material of the electrical skin contact element partially or completely penetrates the fabric of the textile product from the inside surface of the fabric to the outside surface of the fabric and defines some or all of the conductive region.

12. The textile product of claim 8, wherein the conductive polymer material embedded in the pores of the fabric is a product of a process that includes saturating the fabric pores with non-cured conductive polymer and then curing the conductive polymer.

13. A textile product configured to be worn on a body of a wearer, the textile product having an outside surface facing away from the wearer's body and an inside surface configured for skin contact with the wearer's body, the textile product comprising:
one or more integrated sensors, each having an inside portion disposed on the inside surface and an outside portion disposed on the outside surface:
the inside portion comprising an electrical skin contact element having a first side configured for skin contact with the wearer's body over an entirety of the first side, and a second side opposite the first side, the electrical skin contact element partially or completely arranged on the inside surface of the textile product, the electrical skin contact element comprising an extensible electrode defining the entirety of the first side and including an extensible plastic material comprising conductive particles or graphene;
the outside portion comprising at least one extensible conductive element mounted on an outside of the textile product and in electrical communication with the electrical skin contact element; and
wherein one of:
(a) the textile product has at least one opening extending from the outside surface to the inside surface of the textile product and defining an area, the electrical skin contact element first side defining a first area larger than the area defined by said opening and the second side defining a second area equal to the first area, the second side of the electrical skin contact element adhered to the textile product around said opening and directly connected to the at least one extensible conductive element adjacent the opening via a connection consisting of a conductive polymer material disposed in the area defined by the opening; or
(b) the textile product comprises a fabric having an inside surface and an outside surface with pores extending between the inside surface and the outside surface, the fabric having a conductive region comprising a conductive polymer material embedded in the pores of the fabric in an area of the fabric extending between the inside surface of the fabric and the outside surface of the fabric, the at least one extensible conductive element directly connected to the conductive polymer material on the outside surface of the fabric in said conductive region, the conductive region providing a sole electrical connection configured to conduct a current or voltage between the at least one extensible conductive element and the electrical skin contact element through the fabric of the textile product between the inside surface of the fabric and the outside surface of the fabric.

14. The textile product of claim 13, wherein the extensible electrode has an elastic extensibility of at least 10%.

15. The textile product of claim 13, wherein the extensible electrode has an elastic extensibility of at least 20%.

16. The textile product of claim 13, wherein the extensible electrode has an elastic extensibility of at least 30%.

17. The textile product of claim 13, wherein the skin contact element comprises a sensor.

18. The textile product of claim 17, wherein the sensor is selected from the group consisting of: an optical sensor, a pressure sensor, a temperature sensor, a strain sensor, a planar sensor, and a combination thereof.

19. The textile product of claim 13, wherein the conductive polymer material is extensible.

20. The textile product of claim 13, wherein the skin contact element comprises an actuator.

21. The textile product of claim 13, wherein a conductive component of the extensible conductive element comprises wire, including one or more metal undulating or sinusoidal wires, or wherein one or more extensible cores wrapped with metal wires.

22. The textile product of claim 13, comprising a plurality of individual or twisted metallic wires in pairs as a conductor component of the at least one extensible conductive element, each of which is provided with an insulation covering.

23. The textile product of claim 22, wherein the wire insulation covering has a color, and at least one first wire is separately electrically controllable from at least one second wire and has a different color insulation covering than the at least one second wire.

24. The textile product of claim 13, wherein the at least one conductive element is glued, laminated or covered with a laminated tape on the outside of the textile product.

25. The textile product of claim 13, wherein the at least one extensible conductive element is attached in a flat seam to the outside of the textile product, or wherein the at least one extensible conductive element is dimensioned for use with a flat seam sewing machine.

26. The textile product of claim 13, wherein the sensor comprises an electrochemical or optical sensor.

27. A method of using the textile product of claim 13, comprising measuring a heart rate, producing an electrocardiogram, applying stimulation or stimulation currents, or measuring brain currents of a wearer of the textile product.

28. A process for manufacturing the textile product of claim 13, comprising the steps of:
   (a) forming the opening or the conductive region in the textile material;
   (b) arranging the electrical skin contact element partially or completely on the inside surface of the textile product;
   (c) attaching a dissipative element in the form of an extensible conductive textile element to the outside surface of the textile product; and
   (d) making contact between the extensible conductive element and the electrical skin contact element in the conductive region or adjacent the opening.

29. The process of claim 28, wherein in step (a), the opening is created in the textile material, an adhesive is applied around the opening on one side of the textile material, a carrier covering the opening is provided on the other side of the opening; the skin electrical contact element is applied to the adhesive and the carrier; and the carrier is removed.

30. The process of claim 28, comprising covering the skin contact element and a contact region of the skin contact element used for creating the contact with non-conductive material.

31. The process of claim 28, wherein in step (a) the opening is formed in the textile material; and in step (d) the skin contact element is connected via a conductive material to metallic wires of the extensible conductive element, before in steps (b) and (c) the skin contact element is connected to the conductive element or a part thereof is inserted through the opening and then adhered to the inside by means of a non-conductive material.

32. The process of claim 28, wherein in step (a) for forming the conductive region in the textile material, at least a portion of an extensible textile material is impregnated with electrode material or conductive material, which is extensible after hardening and contains conductive particles, and the conductive region on the outside of the textile material is connected to a metallic core of a conductive ribbon and the electrode material or the conductive material is hardened, and then a skin contact element is applied to the inside of the textile material.

* * * * *